(12) United States Patent
Funaki et al.

(10) Patent No.: US 8,349,387 B2
(45) Date of Patent: Jan. 8, 2013

(54) METHOD FOR PRODUCTION OF COATED PREPARATIONS

(75) Inventors: Takeshi Funaki, Hyogo (JP); Tatsumori Yoshida, Hyogo (JP)

(73) Assignee: Shionogi & Co., Ltd., Osaka (JP)

( * ) Notice: Subject to any disclaimer, the term of this patent is extended or adjusted under 35 U.S.C. 154(b) by 422 days.

(21) Appl. No.: 12/733,324

(22) PCT Filed: Aug. 28, 2008

(86) PCT No.: PCT/JP2008/065357
§ 371 (c)(1),
(2), (4) Date: Mar. 23, 2010

(87) PCT Pub. No.: WO2009/028583
PCT Pub. Date: Mar. 5, 2009

(65) Prior Publication Data
US 2010/0203228 A1    Aug. 12, 2010

(30) Foreign Application Priority Data

Aug. 29, 2007 (JP) ................................ 2007-222566

(51) Int. Cl.
*A61K 9/16* (2006.01)
*A61K 9/28* (2006.01)
*B05D 3/00* (2006.01)
*B05D 7/00* (2006.01)

(52) U.S. Cl. .......................... 427/2.14; 427/212; 524/543

(58) Field of Classification Search ................ 427/2.14, 427/212; 524/543
See application file for complete search history.

(56) References Cited

U.S. PATENT DOCUMENTS
2006/0229383 A1    10/2006 Noami et al.
2010/0203228 A1*   8/2010  Funaki et al. ............... 427/2.14

FOREIGN PATENT DOCUMENTS
JP         2007-22938        2/2007

OTHER PUBLICATIONS

International Search Report issued Oct. 7, 2008 in International (PCT) Application No. PCT/JP2008/065357.
Toshiro Fujii et al., "Development of a New Coating Agent, PVA Copolymer", Pharm Tech Japan, 2005, vol. 21, No. 2, pp. 257-261, with partial translation.
Makoto Noami et al., "Investigation on Functionality of a New Coating Agent, a PVA Copolymer", Abstracts of the 21st Symposium on Particulate Preparations and Designs, 2004, vol. 21st, pp. 1-4, with partial translation.
Toshiharu Uramatsu et al., "Investigation on Properties of a New PVA Copolymer", Proceedings of the 124th Annual Meeting of the Pharmaceutical Society of Japan, 2004, 30[P2] 111-332, with partial translation.
International Preliminary Report on Patentability and Written Opinion of the International Searching Authority issued Mar. 30, 2010 in International (PCT) Application No. PCT/JP2008/065357.

* cited by examiner

*Primary Examiner* — Timothy Vanoy
(74) *Attorney, Agent, or Firm* — Wenderoth, Lind & Ponack, L.L.P.

(57) ABSTRACT

The present invention relates to a method for production of a coated preparation, characterized by coating a core material with a coating solution, the core material comprising an active ingredient, the coating solution comprising a) a resin composition obtained by copolymerization of polyvinyl alcohol having an average polymerization degree of 1300 or less, and at least one polymerizable vinyl monomer in a weight ratio of 6:4 to 9:1, b) water, and c) an organic solvent. The method for production make it feasible to efficiently coat a preparation such as a tablet, a granule, and a fine granule, etc. (a pharmaceutical drug, an animal drug, an agricultural chemicals, a fertilizer, or a food product) with the coating solution comprising a) the composition comprising the polyvinyl alcohol copolymer as the main component, b) water, and c) the organic solvent.

17 Claims, No Drawings

METHOD FOR PRODUCTION OF COATED PREPARATIONS

This application is a U.S. national stage of International Application No. PCT/JP2008/065357 filed Aug. 28, 2008.

TECHNICAL FIELD

The present invention relates to a novel method for production of a coated preparation, in particular relates to a method for production of a coated preparation (a pharmaceutical drug, an animal drug, an agricultural chemical, a fertilizer, or a food product) characterized by coating a core material comprising an active ingredient with a coating solution comprising a) a resin composition comprising a polyvinyl alcohol copolymer as a main component, b) water, and c) an organic solvent.

BACKGROUND ART

Conventionally, polyvinyl alcohol (hereafter often abbreviated as PVA) is frequently used as a dispersant, an adhesive, a sizing agent, a film, a paper processing agent, a coating agent, etc. in various kinds of fields. For example, the use of partially saponified PVA as a coating agent is known, since it has water-solubility and film-forming property. However, when PVA is used in a spray method, which is a usual coating method, significant spinnability of PVA makes coating difficult (PVA is sprayed into a spiderweb form, not into a fine mist); thus the use of PVA as a coating agent in a spray method is hardly given a practical application.

In order to solve the above-mentioned problem, a coating composition comprising a PVA copolymer as a main component is suggested in WO 2005/019286 and JP-A 2007-22938. These documents also disclose a method for coating a pharmaceutical preparation such as a tablet, a granule, a fine granule, etc. with an aqueous solution of the above-mentioned coating composition. However, this method has problems: while the coating agent is sprayed, each unit of such a tablet, granule, or fine granule combines and sticks together, and subsequently the film coating peels back; in particular, when the spray rate of the coating solution is increased, the coating yield significantly decreases, and consequently a longer coating time is required.

SUMMARY OF INVENTION

Technical Problem

It is an object of the present invention to provide a method for efficient production of a coated preparation by using a coating solution comprising a) a composition comprising a PVA copolymer as a main component, b) water, and c) an organic solvent.

Solution to Problem

The inventors of the present invention, as a result of repeating diligent research to solve the above-mentioned problems, have found that coating can be efficiently carried out by using a coating solution comprising a) a resin composition obtained by copolymerization of PVA having an average polymerization degree of 1300 or less, and at least one polymerizable vinyl monomer in a weight ratio of 6:4 to 9:1, b) water, and c) an organic solvent. Thus, the present invention has been completed.

In other words, the present invention relates to;

[1] a method for production of a coated preparation, characterized by coating a core material with a coating solution, the core material comprising an active ingredient, the coating solution comprising a) a resin composition obtained by copolymerization of PVA having an average polymerization degree of 1300 or less, and at least one polymerizable vinyl monomer in a weight ratio of 6:4 to 9:1, b) water, and c) an organic solvent;

[2] the method for production according to the above-mentioned [1], wherein the PVA has an average polymerization degree of 900 or less;

[3] the method for production according to the above-mentioned [1], wherein the PVA has an average polymerization degree of 200 to 600;

[4] the method for production according to any of the above-mentioned [1] to [3], wherein the PVA is partially saponified PVA;

[5] the method for production according to any of the above-mentioned [1] to [4], wherein the polymerizable vinyl monomer is selected from the group consisting of acrylic acid, methacrylic acid, methyl acrylate, ethyl acrylate, butyl acrylate, isobutyl acrylate, methyl methacrylate, ethyl methacrylate, butyl methacrylate, and isobutyl methacrylate;

[6] the method for production according to any of the above-mentioned [1] to [5], wherein the concentration of the organic solvent in the coating solution is 5% w/w to 50% w/w;

[7] the method for production according to the above-mentioned [6], wherein the concentration of the organic solvent in the coating solution is 10% w/w to 30% w/w;

[8] the method for production according to any of the above-mentioned [1] to [7], wherein the viscosity of the coating solution is 10 mPa·s to 400 mPa·s;

[9] the method for production according to any of the above-mentioned [1] to [8], wherein the resin composition is a copolymer of partially saponified PVA having an average polymerization degree of 300 to 500, methyl methacrylate, and acrylic acid;

[10] the method for production according to any of the above-mentioned [1] to [9], wherein the weight ratio of the partially saponified PVA having an average polymerization degree of 300 to 500, methyl methacrylate, and acrylic acid in copolymerization is 60-90:7-38:0.5-12;

[11] the method for production according to any of the above-mentioned [1] to [10], wherein coating is performed at an air temperature of 30° C. to 100° C.;

[12] the method for production according to any of the above-mentioned [1] to [11], wherein the coated preparation is a pharmaceutical drug, an animal drug, an agricultural chemical, a fertilizer, or a food product;

[13] the method according for production to the above-mentioned [12], wherein the coated preparation is a tablet, a granule, or a fine granule;

[14] the method for production according to any of the above-mentioned [1] to [13], wherein the organic solvent is at least one selected from the group consisting of ethanol, methanol, acetone, and methylene chloride;

[15] a coating solution comprising a) a resin composition obtained by copolymerization of PVA having an average polymerization degree of 1300 or less, and at least one polymerizable vinyl monomer in a weight ratio of 6:4 to 9:1, b) water, and c) an organic solvent;

[16] a method for preventing each unit of a coated preparation from sticking together, characterized by coating a core material with a coating solution, the core material comprising an active ingredient, the coating solution comprising a) a resin composition obtained by copolymerization of PVA having an average polymerization degree of 1300 or less, and at least one polymerizable vinyl monomer in a weight ratio of 6:4 to 9:1, b) water, c) and an organic solvent; and,

[17] the method according to the above-mentioned [16], wherein the coated preparation is a pharmaceutical drug, an animal drug, an agricultural chemical, a fertilizer, or a food product.

Advantageous Effects of Invention

The method of the present invention can efficiently coat a preparation such as a tablet, a granule, and a fine granule, etc. (a pharmaceutical drug, an animal drug, an agricultural chemical, a fertilizer, or a food product) with a coating solution comprising a) a composition comprising a PVA copolymer as a main component, b) water, and c) an organic solvent; therefore, this method is suitable for mass production of a coated preparation.

DESCRIPTION OF EMBODIMENTS

The resin composition of the present invention resulting from copolymerization of PVA having an average polymerization degree of 1300 or less and at least one polymerizable vinyl monomer in a weight ratio of 6:4 to 9:1 (hereinafter often abbreviated as PVA copolymer) can be produced according to a method known per se.

Examples of the method for producing such a PVA copolymer include a method described in WO 2005/019286. Specific examples of the method include radical polymerization such as solution polymerization, suspension polymerization, emulsion polymerization, and bulk polymerization, etc., all of which are methods known per se. These methods can be carried out under usual polymerization conditions. The polymerization reaction is usually carried out in water, an organic solvent (for example, methanol, ethanol, cellosolve, carbitol), or a mixture thereof in the presence of a polymerization initiator, and if necessary, in the presence of a reducing agent (for example, sodium erythorbate, sodium metabisulfite, ascorbic acid); a chain transfer agent (for example, 2-mercaptoethanol, α-methylstyrene dimer, 2-ethylhexyl thioglycolate, lauryl mercaptan); and/or a dispersing agent (for example, a surfactant such as sorbitan ester and lauryl alcohol). A removing method of an unreacted monomer, a drying method, a crushing method, etc. is also carried out in a known method with no particular limitation.

The PVA as a raw material of the PVA copolymer of the present invention has an average polymerization degree of about 200 to 1300, preferably about 200 to 900, more preferably about 200 to 600, and most preferably about 300 to 500. The PVA also may be partially saponified PVA having a saponification degree of about 60 mol % or more, preferably about 78 mol % to 96 mol %. The saponified PVA can be produced by radical polymerization of vinyl acetate, and subsequently suitable saponification of the vinyl acetate obtained. Production of desired PVA can be achieved by suitably controlling the degree of polymerization and saponification by a method known per se.

Alternatively, the partially saponified PVA may be a commercially-available product. Preferred examples of the commercially-available product of the PVA include GOHSENOL EG-05 (NIPPON GOHSEI Co., Ltd.), GOHSENOL EG-25 (NIPPON GOHSEI Co., Ltd.), PVA203 (Kuraray Co., Ltd.), PVA204 (Kuraray Co., Ltd.), PVA205 (Kuraray Co., Ltd.), JP-04 (JAPAN VAM & POVAL Co., Ltd.), JP-05 (JAPAN VAM & POVAL Co., Ltd.), etc. In the production of the PVA copolymer, which is a main component of the composition in the present invention, PVA as a raw material may be used alone, or in an appropriate combination of two or more kinds thereof having different degrees of polymerization or saponification depending on a purpose. For example, it is feasible to use a mixture of PVA having an average polymerization degree of 300 and PVA having an average polymerization degree of 1300. It is also feasible to use a commercially-available premixed coating agent that comprises PVA.

The PVA used as a raw material in the present invention may be various kinds of modified PVA. Examples of the modified PVA include amine-modified PVA, ethylene-modified PVA, carboxylic acid-modified PVA, diacetone-modified PVA, thiol-modified PVA, etc. As these modified PVA, a commercially-available product or modified PVA produced by a known method in the art may be used.

Examples of the polymerizable vinyl monomer to be polymerized with the PVA as a raw material include the following: unsaturated carboxylic acids such as acrylic acid, methacrylic acid, crotonic acid, fumaric acid, maleic acid, itaconic acid, etc.; esters of unsaturated carboxylic acids (for example, substituted or unsubstituted alkyl ester, cyclic alkyl ester, polyalkylene glycol ester, etc.); unsaturated nitriles; unsaturated amides; aromatic vinyls; aliphatic vinyls; unsaturated bond-containing heterocyclic compounds, etc; and salts thereof (for example, alkali metal salt, ammonium salt, alkylamine salt, etc.). Unsaturated carboxylic acids and esters of unsaturated carboxylic acids are preferred. Specific examples thereof include the following:

(1) acrylic acid esters, for example, methyl acrylate, ethyl acrylate, butyl acrylate, isobutyl acrylate, cyclohexyl acrylate, 2-ethylhexyl acrylate, hydroxyethyl acrylate, polyethylene glycol acrylate (ester of polyethylene glycol and acrylic acid), polypropylene glycol acrylate (ester of polypropylene glycol and acrylic acid), etc.;

(2) methacrylic acid esters, for example, methyl methacrylate, ethyl methacrylate, butyl methacrylate, isobutyl methacrylate, cyclohexyl methacrylate, 2-ethylhexyl methacrylate, hydroxyethyl methacrylate, polyethylene glycol methacrylate (ester of polyethylene glycol and methacrylic acid), etc.;

(3) unsaturated nitriles, for example, acrylonitrile, methacrylonitrile, etc.;

(4) unsaturated amides, for example, acrylamide, dimethylacrylamide, methacrylamide, etc.;

(5) aromatic vinyls, for example, styrene, α-methyl styrene, etc.;

(6) aliphatic vinyls, for example, vinyl acetate, etc.; and (7) unsaturated bond-containing heterocyclic compounds, for example, N-vinyl pyrrolidone, acryloyl morpholine, etc.

It is preferable to use acrylic acid, methacrylic acid, methyl acrylate, ethyl acrylate, butyl acrylate, isobutyl acrylate, methyl methacrylate, ethyl methacrylate, butyl methacrylate, or isobutyl methacrylate.

The polymerizable vinyl monomer alone, or in combination of two or more, can be copolymerized with PVA. Regarding a preferable combination, it is preferable to copolymerize PVA with a mixture of acrylic acid and methacrylic acid ester (for example, methyl methacrylate, etc.). The weight ratio of the PVA and the polymerizable vinyl monomer in the copolymerization is about 6:4 to about 9:1, preferably about 8:2. When acrylic acid and methyl methacrylate are used as polymerizable vinyl monomers, the weight ratio of the PVA and the polymerizable vinyl monomers is about 3:7 to about 0.5:9.5, preferably about 1.25:8.75. A preferable PVA copolymer used as a main component of the coating composition in the present invention is a copolymer of PVA (an average polymerization degree of about 200 to 1300), methyl methacrylate, and acrylic acid. The weight ratio of each component is about 60-90:7-38:0.5-12, preferably about 80:17.5:2.5.

A weight ratio of PVA, methyl methacrylate, and acrylic acid used in copolymerization is 60-90:7-38:0.5-12, which is the same as the weight ratio of PVA, methyl methacrylate, and acrylic acid in the resulting copolymer. The weight ratio can be determined by nuclear magnetic resonance (NMR).

A polymerization initiator used in the art can be used. Examples of the polymerization initiator include inorganic peroxides such as potassium persulfate, ammonium persulfate, hydrogen peroxide, etc.; organic peroxides such as peracetic acid, tertiary butyl hydroperoxide, di-n-propyl peroxydicarbonate, etc.; azo compounds such as 2,2'-azobis(2-amidinopropane)hydrochloride, 2,2'-azobis(2,4-dimethylvaleronitrile), etc.

The concentration of the organic solvent in the coating solution according to the present invention is not particularly limited provided that a separation of the organic solvent from water does not occur. The concentration is usually about 5% w/w to 50% w/w, preferably about 7.5% w/w to 40% w/w, more preferably about 10% w/w to 30% w/w. If the concentration of the organic solvent is too low, the coating solution will not be able to exert its effect of preventing each unit of a pharmaceutical drug or an animal drug from sticking together. If the concentration of the organic solvent is too high, the viscosity of the coating solution will become high, the coating solution will not equally mix with water, and consequently spraying of the coating solution will become difficult.

The organic solvent used for the coating solution according to the present invention is not particularly limited provide that the organic solvent is commonly used for a coating operation. Specific examples of the organic solvent include alcohol (for example, ethanol, methanol, etc.), acetone, methylene chloride, etc. The solvent may be used alone, or in combination of two or more. Preferred examples include ethanol.

The amount of the above-mentioned resin composition contained in the coating solution comprising the above-mentioned resin composition, water, and an organic solvent (hereinafter often abbreviated as a "coating solution") is about 4% w/w to 20% w/w of the total mixed solution, preferably about 6% w/w to 17% w/w, more preferably about 8% w/w to 15% w/w. If the amount of the resin composition is too small, the amount of the solvent in the coating solution will increase, and consequently a longer coating time will be required. If the amount of the resin composition is too large, the viscosity of the coating solution will become high, and consequently each unit of a coated preparation will stick together.

The viscosity of the above-mentioned coating solution means a viscosity determined at a rotational speed of 60 rpm, and at a temperature of 25° C. according to the method for determining viscosity (JIS K 7117-2) in Japanese Industrial Standards (JIS). The viscosity is usually about 10 mPa·s to 400 mPa·s, preferably about 10 mPa·s to 250 mPa·s, more preferably about 10 mPa·s to 200 mPa·s The viscosity can be determined with a commercially-available viscometer, for example, the B-type viscometer (TOKYO KEIKI INC.). If the viscosity of the coating solution is too high, each unit of a coated preparation will stick together.

A type of the coated preparation according to the present invention is not particularly limited, but the coated preparation is preferably a pharmaceutical drug, further preferably a tablet, a granule, or a fine granule, particularly preferably a tablet. The tablet is usually about 4 mm to 12 mm, preferably about 5 mm to 10 mm in diameter, or maximum diameter when the tablet face is not round. Particle size distribution of the granule or the fine granule is usually within the range of 75 µm to 1410 µm, preferably 105 µm to 850 µm.

The method for production according to the present invention comprises the following steps:
1) a step of producing a coating solution by mixing a resin composition, water, and an organic solvent; and
2) a step of coating a core material comprising an active ingredient with the coating solution obtained by the process 1).

The method for the coating is preferably a coating method for a pharmaceutical drug, and spray coating is more preferable. In the process 1), preferably, firstly a resin composition is dissolved or suspended in water, and then an organic solvent is added. The coating solution produced by the process 1) can prevent each unit of a preparation from sticking together. Also, the spray coating can be carried out onto the surface of a preparation that is continuously fluidized and agitated with a known method. For example, the spray coating can be carried out with film-coating apparatus. For a pharmaceutical tablet, specific examples of the film-coating apparatus include a pan coater etc.; for example, Hi-Coater (Freund Corporation), Aqua Coater (Freund Corporation), New Hi-Coater (Freund Corporation), etc. For a pharmaceutical granule, a pharmaceutical fine granules, etc., general examples include a fluidized bed granulator-coater, a combined granulator-coater, a centrifugal fluid-bed granulator-coater etc.; for example, Flow Coater (Freund Corporation), Spir-A-Flow (Freund Corporation), CF-Granulator (Freund Corporation), etc.

The spray rate during coating according to the present invention (hereinafter often abbreviated as a spray rate), in the case of using a Hi-Coater Lab (pan volume: about 1 L, Freund Corporation), a ventilated coating pan, is usually about 0.8 g/min to 4.5 g/min, preferably about 1.0 g/min to 4.0 g/min, more preferably about 1.3 g/min to 3.0 g/min. In the case of using an Aqua Coater AQC-80 (pan volume: about 60 L, Freund Corporation), a ventilated coating pan, the spray rate is usually about 10 g/min to 80 g/min, preferably about 15 g/min to 65 g/min, more preferably about 20 g/min to 50 g/min. If the spray rate is too low, a longer coating time will be required, and production efficiency will decrease. If the spray rate is too high, each unit of a preparation will stick together. The process air temperature into the coating pan during spray coating is, independently of types of coaters, usually 30° C. to 100° C., preferably 40° C. to 90° C., more preferably 50° C. to 80° C. If the temperature is too low, insufficiency of drying on film coatings will cause sticking and peeling of the film coatings, and consequently decrease the yield. If the temperature is too high, excessive of dryness will decrease the adhesion rate of the coating onto the tablets after spraying, and consequently a longer coating time will be required.

The active ingredient in the core material according to the present invention is not particularly limited provided that the active ingredient can be administered orally, and any active ingredient may be used.

In cases where the coated preparation according to the present invention is a pharmaceutical drug, examples of the active ingredient contained in the core material include antibiotics, chemotherapeutic drugs, hypnotics and sedatives, antipsychotic drugs, anxiolytics, antiepileptics, antipyretics, antiparkinson drugs, neuroleptic drugs, skeletal muscle relaxants, autonomic nervous system drugs, antispasmodics, cardiotonic drugs, antiarrhythmic drugs, diuretics, hypotensive drugs, capillary stabilizers, vasoconstrictors, vasodilators, antihyperlipemic drugs, antitussives and expectorants, bronchodilators, stegnotics, intestinal drugs, anti peptic ulcer drugs, stomachics and digestants, antacids, cholagogues, gastrointestinal drugs, vitamin supplements, nutritional tonics, drugs for liver diseases, antipodagrics, antidiabetic drugs, anti-tumor drugs, antihistamines, galenicals, drugs for osteoporosis, etc. The active ingredient is not particularly limited provide that the active ingredient is a pharmacologically active ingredient that can be administered orally, and any active ingredient may be used. The film coating comprising a PVA copolymer has a lower oxygen permeability than usual film coatings. Therefore, even when a preparation comprises an active ingredient that is vulnerable to oxygen, the active ingredient will be prevented from degradation, and will provide sufficient pharmacological activity.

The "core material" according to the present invention means a solid material before coating. The solid material before coating is not particularly limited, and examples of a suitable solid material include a tablet before coating (hereinafter often abbreviated as an "uncoated tablet"), a granule before coating (hereinafter often abbreviated as an "uncoated granule"), or a fine granule before coating (hereinafter often abbreviated as an "uncoated fine granule"), etc.

The uncoated tablet according to the present invention may be any tablet produced by a known method. Specific examples of a suitable method for production include the following:

a) a method for production in which an active ingredient alone, or an active ingredient equally mixed with a suitable additive such as an excipient, a binder, a disintegrant, or other additives, is granulated by a suitable known method, added with a lubricant etc., and compressed into a tablet;

b) a method for production in which a granule that comprises an active ingredient alone, or a granule that comprises an active ingredient equally mixed with a suitable additive such as an excipient, a binder, a disintegrant, or other additives, is directly compressed into a tablet; and, c) a method for production in which a granule that does not comprise any active ingredient is produced in advance, added with an active ingredient alone, or added with an active ingredient equally mixed with a suitable additive, and compressed into a tablet.

The granule also can be produced by a known method in the art. The uncoated tablet may also be covered with a precoating layer before being coated with a coating solution that comprises a PVA copolymer. A precoating agent known in the art may be used. Examples of the precoating agent include hydroxypropyl methyl cellulose and sucrose, etc.

The uncoated granule or the uncoated fine granule according to the present invention may be any granule or fine granule that can be produced by a known method. Specific examples of the production method include wet granulation, dry granulation, etc. Examples of the wet granulations include extrusion granulation, high shear mixer granulation, spray-drying granulation, fluidized bed granulation, etc.

A wide variety of additives known in the art can be used for the coating solution. Examples of the additives include a plasticizer, a lubricant, a solubilizer, a buffer, a surfactant, etc.; in particular, titanium oxide, talc, precipitated calcium carbonate, gelatin, triethyl citrate, triacetin, polyethylene glycol, soybean lecithin, gum arabic, light anhydrous silicic acid, crystalline cellulose, calcium hydrogen phosphate, glycerin, lecithin, macrogol, polysorbate 80, sucrose fatty acid ester, sodium lauryl sulfate, etc.

EXAMPLES

The present invention is explained in the following Examples and Comparative Examples; however, the present invention is not limited thereto.

Example 1

(1) Production of Tablets

Tablets with a diameter of 9.5 mm, a weight of 360 mg and in a shape of a dual radius cup, which had the following composition in Table 1, were produced with a rotary tablet press (KIKUSUI SEISAKUSHO LTD.).

TABLE 1

| Component | Weight (mg) |
| --- | --- |
| D-mannitol | 176 |
| Crystalline cellulose | 176 |
| Magnesium stearate | 8 |
| Sum total | 360 |

(2) Production of a Resin Composition

A resin composition was produced by a method described in WO 2005/019286. That is to say, 175.8 g of PVA (GOHSENOLEG-05, the degree of polymerization of 500, the saponification degree of 88%, NIPPON GOHSEI Co., Ltd.) and 582.3 g of deionized water were placed in a separable flask equipped with a reflux condenser, a dropping funnel, a thermometer, a nitrogen inlet, and a stirrer. The PVA was dispersed in the water at normal temperature, and then dissolved completely at 95° C. Next, 5.4 g of acrylic acid and 37.3 g of methyl methacrylate were added (the PVA: the polymerizable vinyl monomers (wt %)=100:24.5). The air in the flask was replaced with nitrogen gas, and then the mixture was heated up to 50° C. To the mixture, 8.5 g of tertiary butyl hydroperoxide and 8.5 g of sodium erythorbate were added. The mixture was reacted for 4 hours to give a PVA copolymer. The PVA copolymer was dried and crushed into powders by a usual method to give PVA copolymer powders.

(3) Production of Coated Tablets

The PVA copolymer obtained was gradually added into purified water with stirring to prepare an aqueous PVA copolymer solution of 15% w/w. To the solution, ethanol and purified water were added with stirring so that the concentration of the ethanol was 30% w/w and the concentration of the PVA copolymer was 10% w/w in the resulting aqueous PVA copolymer solution (a coating solution).

600 g of the above-mentioned tablets (equivalent to about 1660 tablets) were placed in a ventilated coating pan (Hi Coater Lab, pan-volume: about 1 L, Freund Corporation) equipped with a two-fluid nozzle. The tablets were heated for a certain period of time on the following conditions: the process air temperature into the coating pan was 60° C.; the process air flow volume into the coating pan was 0.8 m$^3$/min; and the static pressure in the coating pan was 80 Pa. After the tablet bed temperature was set to maintain at 40° C. or higher, the above-mentioned coating solution was sprayed onto the tablets at the spray rate of 2.0 g/min, maintaining the tablet bed temperature of 40° C. or higher, on the following conditions: the spray nozzle diameter was 1.2 mm; the spray air volume was 50 L/min; and the pan speed was 20 rpm. Tablets coated with the PVA copolymer of about 6 mg per tablet were obtained.

After coating, the coated tablets were discharged from the ventilated coating pan. All the coated tablets were visually examined to calculate the yield of good tablets, which was the ratio of the number of good coated tablets to the number of the total coated tablets. The number of the good coated tablets was able to be obtained by subtracting the number of defective tablets that had developed film-peeling or sticking together, from the number of the total coated tablets.

As a result, film-coated tablets with good appearances were obtained with a coating time of 70 minutes. The yield was 98.8%, and defective tablets were few. It was confirmed that coating was efficiently carried out.

Example 2

Coating was carried out in the same manner as Example 1 except that the concentration of the ethanol in the solvent was 10% w/w. The coating time was 78 minutes and the yield was 96.6%. As a result, it was confirmed that ethanol even at a low concentration was fully effective;

Example 3

Coating was carried out in the same manner as Example 1 except that the concentration of the ethanol in the solvent was 30% w/w and the process air temperature into the coating pan was 48° C. The coating time was 62 minutes and the yield was 99.2%. As a result, it was confirmed that the coating time can be further shortened, and that an active pharmaceutical ingredient that is vulnerable to heat can be coated.

Example 4

Coating was carried out in the same manner as Example 1 except that the spray rate was 3.0 g/min. The coating time was 45 minutes and the yield was 94.9%.

Example 5

To prepare a coating solution at a solid concentration of 10% w/w, a PVA copolymer at a polymerization degree of 500 and titanium oxide were added into purified water with stirring, and then ethanol was added thereto with stirring so that the concentration of the ethanol was 10% w/w.

28800 g of tablets (equivalent to about 80000 tablets) with the composition in Table 1 in Example 1 were placed in a ventilated coating pan (Aqua Coater AQC-80, Pan volume: about 60 L, Freund Corporation) equipped with a two-fluid nozzle. The tablets were heated for a certain period of time on the following conditions: the process air temperature into the coating pan was 65° C.; the supply air volume was 9.5 m³/min; and the exhaust air volume was 15.0 m³/min. The tablet bed temperature was set to maintain at 40° C. or higher. After that, the coating solution was sprayed onto the tablets on the following conditions: the spray nozzle diameter was 1.2 mm; the spray air volume was 140 L/min; and the pan speed was 9 rpm. Meanwhile, the spray rate of the coating solution was gradually elevated to confirm the spray rate at which sticking of the tablets and peeling of the film were observed.

As a result, sticking together of the tablets was not observed even at the spray rate of the coating solution of 45 g/min, and film-coated tablets with good appearances were obtained.

Comparative Example 1

Coating was carried out in the same manner as Example 1 except that, without using the ethanol, the aqueous PVA copolymer solution of 10% w/w was used as the coating solution, and that the spray rate was 0.9 g/min. As a result, the yield was 99.5%, and defective tablets were few; however, an extended coating time, 120 minutes, was required.

Comparative Example 2

Coating was carried out in the same manner as Example 1 except that, without using the ethanol, the aqueous PVA copolymer solution of 10% w/w was used as a coating solution, and that the spray rate was 1.9 g/min. As a result, the coating time was 53 minutes. Many coated tablets stuck together and the film peeled back, and the yield was 13.2%.

Comparative Example 3

According to Example 5, coating was carried out in the same manner as the example except that, without using the ethanol, the coating solution at a solid concentration of 10% w/w was used.

As a result, at the spray rate of the coating solution of 20 g/min, sticking together of tablets was observed and film-coated tablets with good appearances could not be obtained.

The above results clearly show that the methods for production in Examples allow the spray rate of the coating solution to be more than twice as fast as that in Comparative Examples, and that blending only a small amount of ethanol into the composition of the coating solution allows a faster spray rate of the coating solution. Efficient coating was confirmed even in the scale-up condition. It was also confirmed that a coated preparation can be efficiently produced even if the coating solution comprises an additive such as titanium oxide.

INDUSTRIAL APPLICABILITY

According to the present invention, a coated preparation can be efficiently produced by the use of a coating solution comprising a) a resin composition obtained by copolymerization of PVA having an average polymerization degree of 1300 or less, and at least one polymerizable vinyl monomer in a weight ratio of 6:4 to 9:1, b) water, and c) an organic solvent.

The invention claimed is:

1. A method for production of a coated preparation, characterized by coating a core material with a coating solution, the core material comprising an active ingredient, the coating solution comprising a) a resin composition obtained by copolymerization of polyvinyl alcohol having an average polymerization degree of 1300 or less, and at least one polymerizable vinyl monomer in a weight ratio of 6:4 to 9:1, b) water, and c) an organic solvent.

2. The method for production according to claim 1, wherein the polyvinyl alcohol has an average polymerization degree of 900 or less.

3. The method for production according to claim 1, wherein the polyvinyl alcohol has an average polymerization degree of 200 to 600.

4. The method for production according to claim 1, wherein the polyvinyl alcohol is partially saponified polyvinyl alcohol.

5. The method for production according to claim 1, wherein the polymerizable vinyl monomer is selected from the group consisting of acrylic acid, methacrylic acid, methyl acrylate, ethyl acrylate, butyl acrylate, isobutyl acrylate, methyl methacrylate, ethyl methacrylate, butyl methacrylate, and isobutyl methacrylate.

6. The method for production according to claim 1, wherein the concentration of the organic solvent in the coating solution is 5% w/w to 50% w/w.

7. The method for production according to claim 6, wherein the concentration of the organic solvent in the coating solution is 10% w/w to 30% w/w.

8. The method for production according to claim 1, wherein the viscosity of the coating solution is 10 mPa·s to 400 mPa·s.

9. The method for production according to claim 1, wherein the resin composition is a copolymer of partially saponified polyvinyl alcohol having an average polymerization degree of 300 to 500, methyl methacrylate, and acrylic acid.

10. The method for production according to claim 9, wherein the weight ratio of the partially saponified polyvinyl alcohol having an average polymerization degree of 300 to 500, methyl methacrylate, and acrylic acid in copolymerization is 60-90:7-38:0.5-12.

11. The method for production according to claim 1, wherein coating is performed at an air temperature of 30° C. to 100° C.

12. The method for production according to claim 1, wherein the coated preparation is a pharmaceutical drug, an animal drug, an agricultural chemical, a fertilizer, or a food product.

13. The method for production according to claim 12, wherein the coated preparation is a tablet, a granule, or a fine granule.

14. The method for production according to claim 1, wherein the organic solvent is at least one selected from the group consisting of ethanol, methanol, acetone, and methylene chloride.

15. A coating solution comprising a) a resin composition obtained by copolymerization of polyvinyl alcohol having an average polymerization degree of 1300 or less, and at least one polymerizable vinyl monomer in a weight ratio of 6:4 to 9:1, b) water, and c) an organic solvent.

16. A method for preventing each unit of a coated preparation from sticking together, characterized by coating a core material with a coating solution, the core material comprising an active ingredient, the coating solution comprising a) a resin composition obtained by copolymerization of polyvinyl alcohol having an average polymerization degree of 1300 or less, and at least one polymerizable vinyl monomer in a weight ratio of 6:4 to 9:1, b) water, and c) an organic solvent.

17. The method according to claim 16, wherein the coated preparation is a pharmaceutical drug, an animal drug, an agricultural chemical, a fertilizer, or a food product.

* * * * *